United States Patent [19]

Faries, Jr. et al.

[11] Patent Number: 5,524,643
[45] Date of Patent: Jun. 11, 1996

[54] METHOD AND APPARATUS FOR DETECTION OF LIQUID AND LEAKS IN SURGICAL DRAPES USED WITH SURGICAL EQUIPMENT

[75] Inventors: Durward I. Faries, Jr., McLean; Mark Licata, Richmond, both of Va.

[73] Assignee: O.R. Solutions, Inc., Chantilly, Va.

[21] Appl. No.: 433,852

[22] Filed: May 2, 1995

[51] Int. Cl.⁶ .............................. A61B 19/00; A47K 1/06
[52] U.S. Cl. .............................. 128/849; 4/655
[58] Field of Search .................. 128/849–856; 4/DIG. 18, 452, 48.4, 580, 655; 62/66

[56] References Cited

U.S. PATENT DOCUMENTS

| | | | |
|---|---|---|---|
| 4,393,659 | 7/1983 | Keyes | 62/66 |
| 4,474,016 | 10/1984 | Winchell | |
| 4,934,152 | 6/1990 | Templeton | 128/846 |
| 5,163,299 | 11/1992 | Faries | 128/846 |
| 5,331,280 | 7/1994 | Zur | 324/309 |
| 5,333,326 | 8/1994 | Faries | 604/113 |
| 5,429,801 | 7/1995 | Faries, Jr. et al. | |

Primary Examiner—Michael A. Brown

[57] ABSTRACT

The present invention is directed to a method and apparatus for preventing damage to drapes and to heating and cooling mechanisms used in conjunction with apparatus for containing and thermally treating sterile liquid, and to preserving the sterile field when using such apparatus. A surgical drape is combined with a sensor, preferably attached to the drape, to detect whether or not liquid is present in a drape container conforming to a heating/cooling basin. An alternative embodiment employs sensors at opposite surfaces of the drape to measure conductance and, thereby, leakage through the drape. A microprocessor in each embodiment receives a signal representing, for example, an electrical conductance measurement from the sensors and determines if liquid is present, or alternatively if the conductance is sufficient to represent the presence of a leak. If liquid is not present or a leak is determined to exist, the microprocessor disables a temperature controller for the basin to prevent damage to the drape and heating and cooling mechanisms.

22 Claims, 3 Drawing Sheets

METHOD AND APPARATUS FOR DETECTION OF LIQUID AND LEAKS IN SURGICAL DRAPES USED WITH SURGICAL EQUIPMENT

BACKGROUND OF THE INVENTION

1. Technical Field

The present invention pertains to improvements in methods and apparatus for heating or cooling sterile surgical liquids and collecting surgical sterile slush. In particular, the invention is an improvement of the methods and apparatus disclosed in U.S. Pat. Nos. 4,393,659 (Keyes et al), 4,934,152 (Templeton), 5,163,299 (Faries, Jr. et al), 5,331,280 (Faries, Jr. et al), 5,333,326 (Faries, Jr. et al), and copending U.S. patent application Ser. No. 08/336,423, filed Oct. 20, 1994. The disclosures in those patents and applications are expressly incorporated by reference herein in their entireties.

2. Discussion of the Prior Art

The above-referenced Keyes et al patent discloses a surgical slush producing system having a cabinet with a heat transfer basin at its top surface. A refrigeration mechanism in the cabinet takes the form of a closed refrigeration loop including: an evaporator in heat exchange relation to the outside surface of the heat transfer basin; a compressor; a condenser; and a refrigeration expansion control, all located within the cabinet. A separate product basin is configured to be removably received in the heat transfer basin. Spacers, in the form of short cylindrical stubs or buttons, are arranged in three groups spaced about the heat transfer basin and projecting into the heat transfer basin interior to maintain a prescribed space between the two basins. During use, that space contains a thermal transfer liquid, such as alcohol or glycol, serving as a thermal transfer medium between the two basins. A sterile drape, impervious to the thermal transfer medium, is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to remove congealed sterile material from the product basin side to thereby form a slush of desired consistency within the product basin. Some users of the system employ the scraping tool to chip the solid pieces from the basin side.

As noted in the above-referenced Templeton patent, the Keyes et al system has a number of disadvantages. In particular, the separate product basin must be removed and re-sterilized after each use. Additionally, the glycol or other thermal transfer medium is highly flammable or toxic and, in any event, complicates the procedure. The Templeton patent discloses a solution to these problems by constructing an entirely new apparatus whereby the product basin is eliminated in favor of a sterile drape impervious to the sterile surgical liquid, the drape being made to conform to the basin and directly receive the sterile liquid. Congealed liquid is scraped or chipped from the sides of the conformed drape receptacle to form the desired surgical slush.

The Faries, Jr. et al U.S. Pat. No. (5,163,299) notes that scraping congealed liquid from the drape is undesirable in view of the potential for damage to the drape, resulting in a compromise of sterile conditions. As a solution to the problem, the patent proposes that the drape be lifted or otherwise manipulated by hand to break up the congealed liquid adhering to the drape. Although this hand manipulation is somewhat effective, it is not optimal, and often is inconvenient and constitutes an additional chore for operating room personnel.

The Faries, Jr. et al U.S. Pat. No. (5,331,820) resolves the problem of manual manipulation of the drape by providing a method and apparatus to automatically remove the congealed liquid adhering to the drape without endangering the integrity of the drape. A flat disk or plate is provided at the bottom of the basin under the drape. The plate is moved in an up and down matter to disengage the congealed liquid from the drape. The plate may be attached to a mechanism below the basin, or to the drape itself as disclosed in copending U.S. patent application Ser. No. 08/336,423.

Templeton further provides an electrical heater disposed at the bottom of the basin to convert the sterile slush to warmed liquid, or to heat additional sterile liquid added to the basin. Templeton describes the need for such warm sterile liquid as occurring after a surgical procedure is completed to facilitate raising the body cavity of the surgery patient back to its normal temperature by contact with the warmed liquid. However, there are a number of instances during a surgical procedure when it is desirable to have simultaneous access to both the sterile warmed liquid and the sterile surgical slush. The Faries, Jr. et al (5,333,326) patent provides a method and apparatus for simultaneously providing separate surgical slush and warmed surgical liquid during a surgical procedure using a single drape for such a unit.

The foregoing patents do not provide a way to prevent damage to the heating and cooling mechanisms when there is no liquid present in the respective basins. Further, the foregoing patents do not provide a way to detect leaks in a surgical drape. Specifically, when insignificant amounts of liquid are present in the basins, the heating and cooling mechanisms operate with little thermal resistance, thereby making burn out of the mechanisms likely. Another consequence is that the drapes are damaged by being attached to the heating or cooling mechanism without having the liquid to absorb the thermal energy. Since only sterile drapes are to be used during surgical procedures, a leak in a surgical drape compromises sterility and contaminates the entire surgical procedure, thereby increasing the risk of injury to the patient.

OBJECTS AND SUMMARY OF THE INVENTION

Accordingly, it is an object of the present invention to provide an apparatus and method to detect the absence of liquid in a drape used to contain fluid by employing a sensor to detect moisture.

It is another object of the present invention to detect leaks in the surgical drape by employing a sensor detecting conductances, and determining whether the conductances are within a range indicative of a leak.

According to the present invention, a drape with sensors is positioned as a drape container in one or more basins on apparatus for thermally treating sterile liquids such that one sensor is located in the drape container toward the bottom of each individual basin. The sensors detect whether liquid is present in each of the drape containers. A microprocessor receives the signals from the sensors and prevents thermal treatment of liquid in drape containers not containing liquid.

In a second embodiment, additional sensors are situated on the drape at the bottom of each basin below the drape so that sensors reside on opposite sides of each drape container.

The sensors detect any conductance residing between them in each individual basin. A microprocessor receives the conductance from the sensors and determines if the conductance is sufficient to indicate an electrical path which is representative of a leak. If a leak is determined to exist, the microprocessor prevents operation of the basin containing the leak.

The above and still further objects, features and advantages of the present invention will be apparent upon consideration of the following detailed description of the specific embodiments thereof, particularly when taken in conjunction with the accompanying drawings wherein like components are designed by like reference numerals.

DESCRIPTION OF THE PREFERRED EMBODIMENTS

The present invention can be applied to various apparatus for providing thermally treated sterile media such as surgical slush machines, liquid warming and cooling systems, and multiple unit machines capable of performing both liquid warming, cooling and slush generation.

Figure 1:
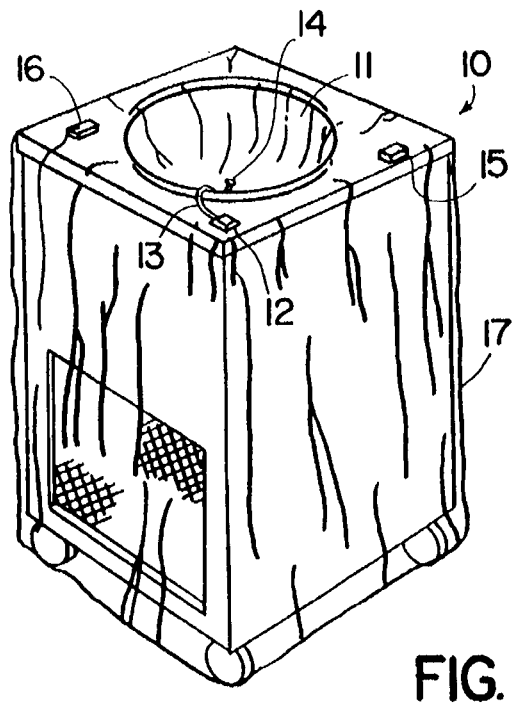
FIG. 1 is a view in perspective of a surgical slush machine and surgical drape according to the present invention.

FIG. 1 illustrates an example of a surgical slush machine including a surgical drape implementing the liquid and leak determination of the present invention. The surgical slush machine includes a cabinet 10 with a top surface having a basin 11 mounted thereon in an appropriately sized recess. Basin 11 is made of thermally conductive material, typically stainless steel, and includes a generally flat bottom wall and a frusto-conical sidewall. A conventional refrigeration unit (not shown) is disposed within cabinet 10 and typically includes a compressor, a condenser and an expansion control unit connected by appropriate fluid conduits in a closed refrigeration loop with an evaporator (not shown). The evaporator is in the form of a coil wound about the exterior surface of basin 11 in thermal transfer relation therewith. When the refrigeration unit is activated by means of an appropriate on-off controller 15 and temperature adjustment control 16, the evaporator cools the sidewall of basin 11 to a temperature substantially below the freezing temperature of the liquid used in forming the sterile slush. A sterile surgical drape 17, preferably transparent, is disposed over the top and sides of cabinet 10 and made to conform to the side wall and bottom of basin 11. The on-off controller 15 and temperature adjustment control 16 are disposed on the top surface of cabinet 10 and are adjustable/controllable manually through drape 17. The portion of surgical drape 17 disposed in the basin serves as a sterile receptacle or drape container for sterile liquid placed therein to be frozen into the described sterile slush.

Drape 17 has a sensor 14 that preferably is affixed thereto and is preferably positioned toward the bottom of basin 11. The sensor may, if desired, be located at a predetermined height above the basin bottom and, thereby serve as a liquid level detector. Sensor 14 is connected to cabinet 10 by way of a drape plug connector 13 plugged into a cabinet receptacle connector 12. The surgical slush machine only operates when drape plug connector 13 is plugged into cabinet receptacle connector 12. Sensor 14 in the preferred embodiment is permanently affixed to the drape by adhesive, ultrasonic welding, or any other suitable manner or means, typically at the time the drape is manufactured. Removable sensor arrangements may also be used.

When the surgical slush machine is in operation, the sterile liquid in the drape receptacle freezes in pieces on the surgical drape covering the sidewalls of the basin. A mechanism for automatically removing the frozen pieces from the surgical drape is disclosed in U.S. Pat. No. 5,331,820, the disclosure of which is expressly incorporated herein. In that patent the drape container sides are moved up and down automatically to loosen attached pieces of frozen saline.

Figure 2:
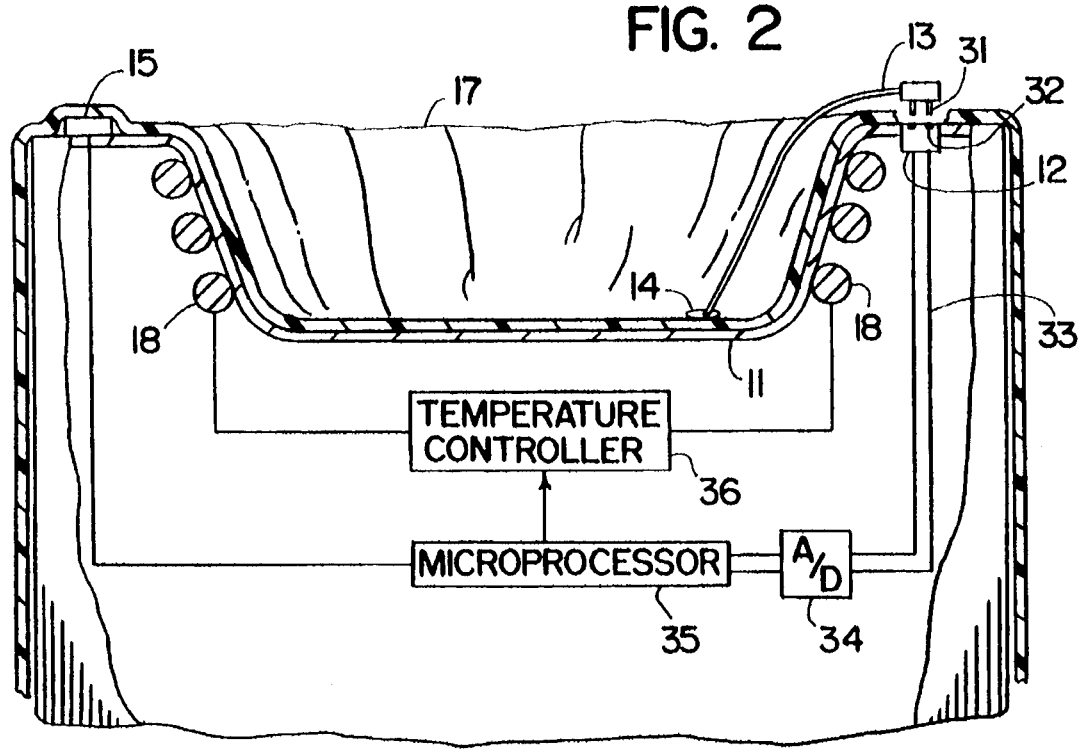
FIG. 2 is a partially diagrammatic view in elevation and partial section of the present invention embedded in the machine of FIG. 1.

FIG. 2 illustrates in greater detail the liquid detection apparatus of the present invention used in a surgical slush machine. Specifically, drape 17 is deployed in basin 11 so as to cause sensor 14 on drape 17 to be positioned generally toward the bottom of basin 11. Drape plug connector 13 plugs into cabinet receptacle connector 12 to couple sensor 14 to a microprocessor 35, via A/D converter 34, to enable operation of the machine. Microprocessor 35 controls electrical application of power to a temperature controller 36 based on an analysis of signals from sensor 14. Temperature controller 36 controls operation of the refrigeration system, including evaporator 18, to adjust the temperature of liquid in basin 11 according to temperature adjustment control 16 (FIG. 1). Power switch 15 controls power to the surgical slush machine.

Sensor 14 comprises two leads between which electrical conductance is measured. If liquid is not present between the leads then zero or insignificant conductance is measured and a signal indicating such is sent to microprocessor 35. Alternatively, the sensor may be implemented in fiber optics whereby optical properties of the sensor measurably vary depending upon its placement in liquid. The sensor detects optical conductivity changes and sends a corresponding signal to microprocessor 35.

In operation, sensor 14 detects the presence or absence of liquid and sends an analog signal to A/D converter 34 via drape plug connector 13. Specifically, drape plug connector 13 is a conventional plug containing pins 31 received in sockets 32 of cabinet receptacle connector 12. Sockets 32 are connected to wires 33 to carry the signal to A/D converter 34. A/D converter 34 converts the analog sensor signal into a corresponding digital signal suitable for application to I/O pins (not shown) of microprocessor 35. If drape plug connector 13 is not plugged into sockets 32 of cabinet receptacle connector 12, microprocessor 35 ultimately receives no signal, or a low amplitude signal, from sensor 14, which is equivalent to zero or insignificant conductance, and inhibits application of power to temperature controller 36. Microprocessor 35 analyzes the converted digital sensor signal, containing either conductance or optical properties, in order to determine if liquid is present in basin 11. If microprocessor 35 determines liquid is not present, microprocessor 35 disables electrical power to temperature controller 36 to prevent damage to the drape and cooling mechanism.

Figure 3A:
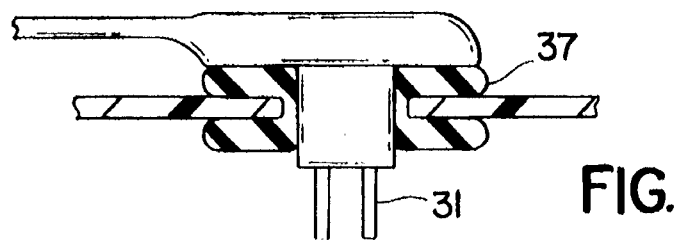
FIG. 3A is a more detailed view in elevation and partial section showing the drape plug connector permanently attached to the drape.
Figure 3B:
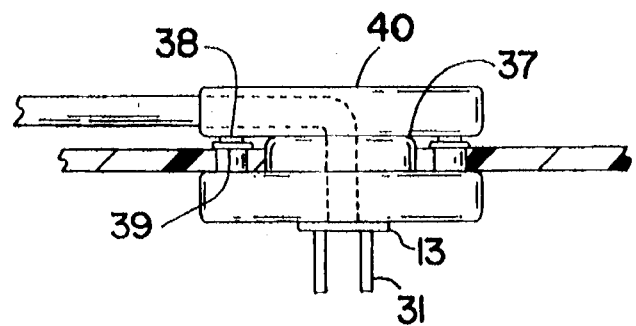
FIG. 3B is a view similar to FIG. 3A of another embodiment of the invention wherein the drape plug connector is removably attached to the drape.

Referring to FIG. 3A, drape plug connector 13 is permanently attached to drape 17 by insertion through an opening in drape 17 surrounded by seals 37. Seals 37 insulate drape 17 to maintain sterility (i.e., to assure no contamination of the sterile field at the exposed surface of the drape). Alternatively, FIG. 3B illustrates drape plug connector 13 being removably attached to drape 17. Drape plug connector 13 is inserted through an opening in drape 17 and attached to drape 17 by snap buttons 38 and is affixed to a holder 40 containing the snap buttons 38 on opposite sides. Snap buttons 38 are inserted into snap receptacles 39 mounted on drape 17 to extend therethrough from opposite sides of the drape at the location where drape plug connector 13 is inserted. Snap receptacles 39 are insulated by seals 37 to maintain sterility of drape 17. Snap buttons 38 and snap receptacles 39 are conventional snap fasteners. Seals 37 may be made of rubber, urethane, silicone, epoxy, acrylic or any other material capable of functioning as a seal to insulate drape 17.

As noted above, sensor 14 may be positioned to serve as a liquid level detector, in which case the liquid in the drape container must be present at the sensed level to permit operation of the system.

Figure 4:
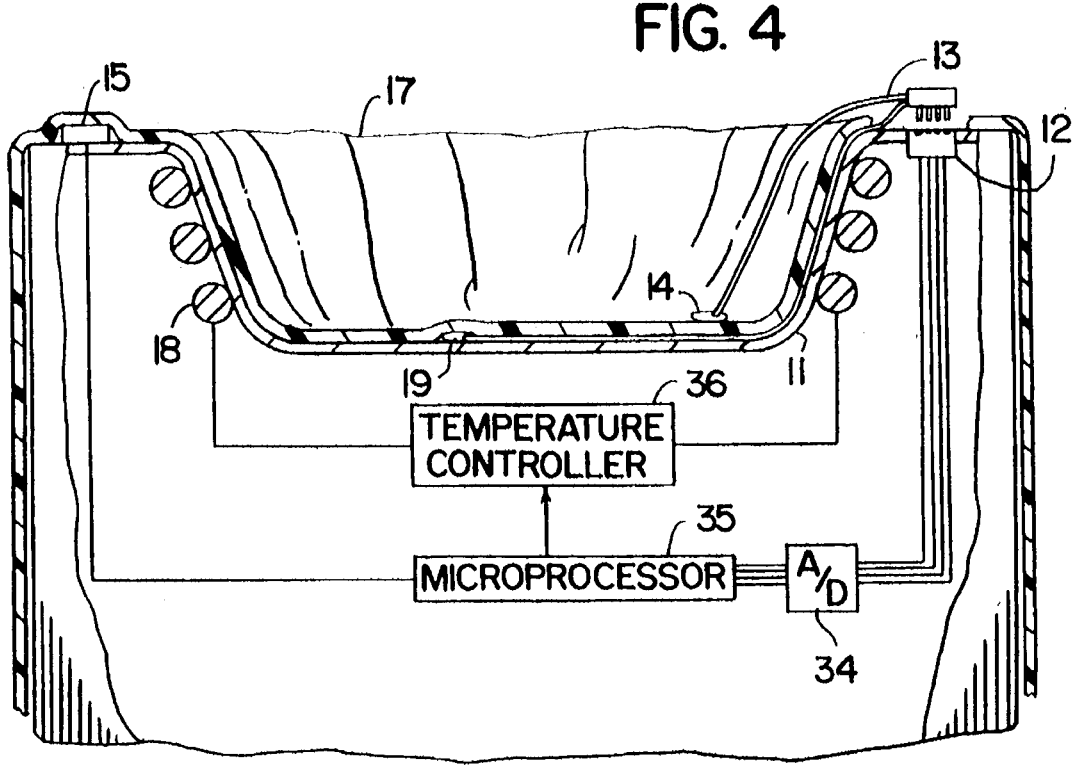
FIG. 4 is a partially diagrammatic view in elevation and partial section of the leak detection embodiment of the present invention embedded in the machine of FIG. 1.

FIG. 4 illustrates a second embodiment of the present invention. Specifically, an additional sensor 19 is employed on the drape so that conductance is measured between sensors 14 and 19 residing on opposite sides of drape 17. Sensor 19 is preferably permanently affixed to drape 17 in the same manner as described above for sensor 14. Sensors 14, 19 measure such conductance and send a signal to A/D converter 34 via drape plug connector 13 through cabinet receptacle connector 12. Drape plug connector 13 may be permanently or removably attached to drape 17 as described above. A/D converter 34 converts analog sensor signals to digital signals for use by microprocessor 35 in analyzing the measure of conductance. The measured conductance signifies whether an electrical path between sensors 14 and 19 has been established, indicating the presence of a leak. If microprocessor 35 determines a leak is present, microprocessor 35 disables electrical power to temperature controller 36 to prevent compromise of liquid sterility and prevent damage to the cooling mechanism.

Figure 5:
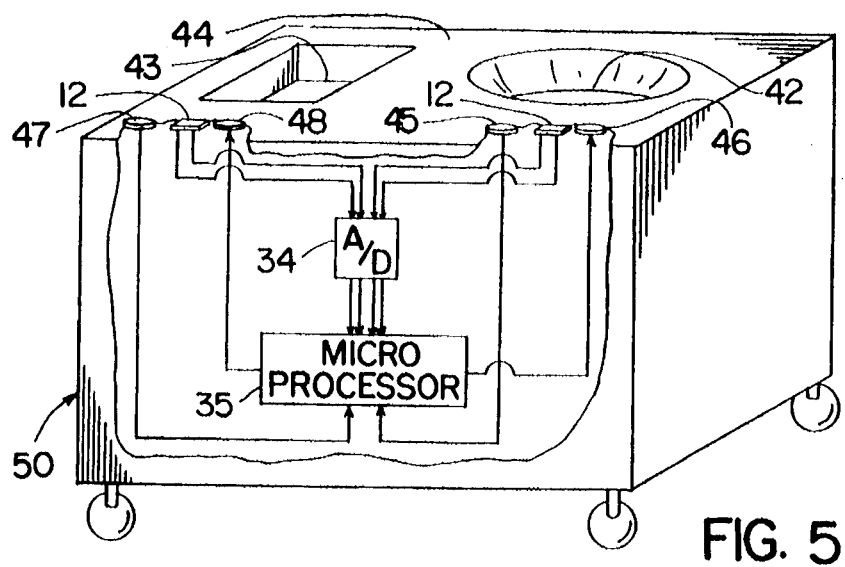
FIG. 5 is a view in perspective of a machine containing both a heating basin and a cooling basin for use with the drape of the present invention.

The embodiments of the present invention are not limited to a single heating or cooling basin. Several heating, cooling or slush basins may be connected for use with a drape varying in size to accommodate all the basins. An example illustrating such multiple basins is shown in FIG. 5. Specifically, an integral assembly 50 includes a cooling basin 42 for slush and a warming basin 43 for liquid recessed into the top surface 44 of a common cabinet. Also disposed within integral assembly 50 are cooling unit power switch 45, a cooling unit temperature controller/indicator 46, a heater power switch 47, a heater unit temperature controller/indicator 48, an A/D converter 34, a microprocessor 35, and cabinet receptacle connectors 12 for receiving sensor data.

Figure 6:
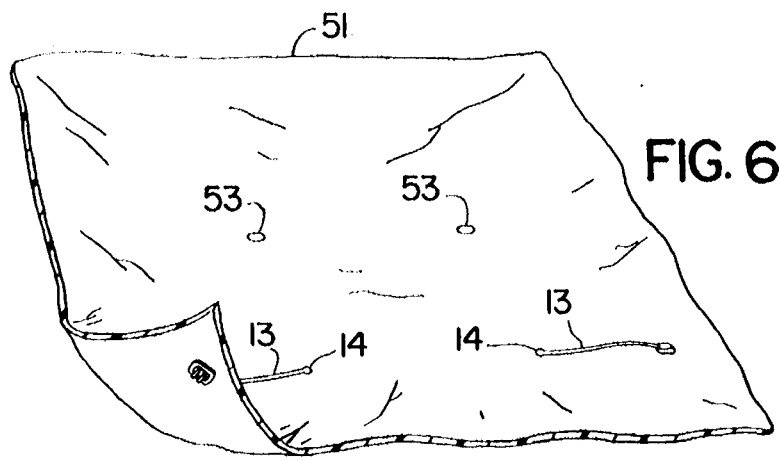
FIG. 6 is a view in plan of a surgical drape of the present invention having particular utility with the machine of FIG. 5.

A sterile surgical drape 51 suitable for covering the entire top surface 44 and to provide drape containers for both basins 42 and 43 is illustrated in FIG. 6. Drape 51 has sensors 14 attached thereto with corresponding drape plug connectors 13. Drape plug connectors 13 are inserted through openings in drape 51 and are permanently or removably attached to drape 51 as described above. Drape 51 has two centering marks or indicia 52, 53 adapted to be placed over the centers of the cooling and warming basins 42 and 43, respectively, during installation of the drape.

Figure 7:
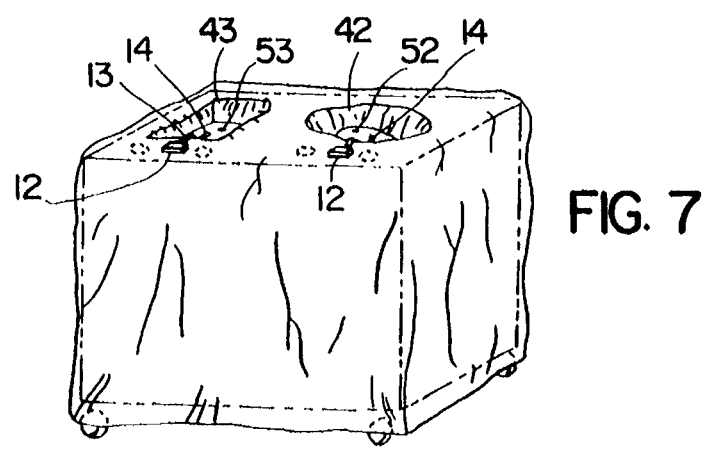
FIG. 7 is a view in perspective of the surgical drape of FIG. 6 deployed on the machine of FIG. 5.

FIG. 7 illustrates the centering indicia 52, 53 properly positioned when drape 51 is pushed down into respective basins until the drape conforms to the basin shapes. Sensors 14 are positioned toward the bottom of basins 42, 43 with drape plug connectors 13 plugged into their corresponding cabinet receptacle connectors 12.

Operation of the liquid detection embodiment of the present invention in the multiple basin machine is substantially similar to the embodiment described above for FIG. 2. Referring to FIGS. 5, 7, microprocessor 35 receives digitally converted sensor signals from sensors 14 via A/D converter 34. Microprocessor 35 determines the basins which do not possess any liquid (or wherein the liquid is not at a minimum predetermined level) based on the conductance measurement of the individual sensors 14, and disables power to only those temperature controllers 46, 48 corresponding to basins where no liquid is present. If a drape plug connector 13 is not connected to cabinet receptacle connector 12, microprocessor 35 receives a signal level representing zero or insignificant conductance from corresponding sensor 14 and power is disabled to the basin whose drape plug connector 13 is not connected.

Leak detection in the multiple basin machine is substantially similar to the embodiment described in FIG. 4. Referring to FIG. 7, additional sensors 19 (not shown) are deployed on drape 51 and positioned at the bottom of basins 42, 43 such that each basin contains one sensor on respective opposite sides of the drape (FIG. 4). The conductance between sensors 19, 14 is measured and the sensors in each basin send a measurement signal through A/D converter 34, to microprocessor 35. Microprocessor 35 determines which conductances from each basin are determinative of a leak, and subsequently disables power to the temperature controllers corresponding to those basins where a leak has been detected. If a drape plug connector 13 is not connected to cabinet receptacle connector 12, microprocessor 35 receives zero or insignificant conductance from corresponding sensor 14 and power is disabled to the basin whose drape plug connector 13 is not connected.

The surgical drapes for all of the above machines are made of material that is impervious to the heated and cooled sterile liquid and slush, and is sufficiently soft and flexible to conform to the walls of basins. Typically, by way of example only, the surgical drape is made of materials commonly used in hospitals for drapes. The drapes may also be made of polyurethane film as disclosed in the aforementioned Templeton Patent. The surgical drapes are designed to be disposable after a single use to assure sterility for each surgical procedure, and are provided pre-sterilized and pre-packaged in a leak proof plastic bag or other sealed container to preserve the sterile nature of the surgical drape during storage.

Microprocessor control is accomplished by software providing conductance determinations and comparisons. The microprocessor may be implemented by virtually all commercially available microprocessor chips as known in the art.

It will be appreciated that the embodiments described and illustrated in the drawings represent only a few of the many ways of implementing detection of liquids and leaks of drape containers in the present invention.

The microprocessor of the leak detection embodiment of the present invention may be utilized to account for absorption of the sterile liquid by the drape material forming in the drape container. For some drape materials this absorption is significant and increases the conductance measured by the sensors through the drape, even though there is no leak, and produces false detections of leaks. The microprocessor may be supplied with liquid and drape material specific hydration tables for the drape to adjust sensitivity of the microprocessor to the conductance measurements and reduce the amount of false detections. Hydration characteristics of drape materials, as a function of time, are known and can easily be programmed into the microprocessor.

The function of the microprocessor may be accomplished by general circuitry, combinational logic or any other switching means used to disable power.

The present invention may include sound or visual indicators notifying when the absence of liquid or a leak is present. Such indicators include an alarm, buzzer, colored light, speech synthesizer or any other indicator used for specifying a condition or state of an object.

The drape plug connector of the present invention may be implemented with various numbers and types of pins, dependent upon the desired resolution or accuracy of the measured conductance. Alternatively, the drape plug connector may be implemented using sockets plugged into corresponding pins in the cabinet receptacle connector to yield the same results.

The drape plug connector of the present invention may be removably attached to the drape by any means capable of fastening the drape plug connector to the drape.

Although the preferred embodiment discloses sensors containing electrical leads and fiber optics, any sensors for measuring conductance or presence of liquid may be implemented according to the present invention.

From the foregoing description it can be appreciated that the invention makes available a novel method and apparatus for detection of liquid and leaks in surgical drapes by measuring and analyzing conductance. In addition, the invention prevents operation of the machine if either the absence of liquid or a leak has been determined to exist.

Having described preferred embodiments of the new and improved method and apparatus for detection of liquid and leaks in surgical drapes, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. An apparatus for detecting the presence of sterile liquid in containers formed by surgical drapes during surgical procedures, said apparatus comprising:

thermal treatment means for thermally treating a liquid and including a basin;

a surgical drape, covering and substantially conforming to said basin to serve as a drape container for said liquid;

sensor means in said drape container for sensing the presence and absence of liquid in contact with said sensor means;

actuable means for operating said thermal treatment means to control a temperature of said basin; and power control means responsive to said sensor means for controlling said thermal treatment means in accordance with the presence and absence of liquid in contact with said sensor means.

2. The apparatus of claim 1 wherein said sensor means is a fiber optic sensor.

3. The apparatus of claim 1 wherein said sensor means includes means for detecting conductance between opposite surfaces of said drape.

4. The apparatus of claim 3 wherein said sensor means includes two sensors affixed to respective surfaces of said drape.

5. The apparatus of claim 1 wherein said power control means disables power to said thermal treatment means in response to said sensor means detecting the absence of a liquid in contact with the sensor means.

6. The apparatus of claim 1 wherein said power control means disables power to said thermal treatment means in response to said sensor means detecting conductance in a range indicative of a leak in said surgical drape.

7. The apparatus of claim 1 wherein said thermal treatment means is operative to cool liquid in said drape container.

8. The apparatus of claim 1 wherein said thermal treatment means produces a heated liquid in said drape container.

9. The apparatus of claim 1 wherein said thermal treatment means comprises at least two separate basins providing heated and cooled liquids, respectively, simultaneously in said separate basins.

10. The apparatus of claim 1 wherein:

said thermal treatment means further includes a plurality of said basins;

said surgical drape covers and substantially conforms to each said basin of said plurality of basins to serve as said drape container for said liquid in each said basin;

said sensor means disposed in each said drape container of each said basin for sensing the presence and absence of liquid in contact with said sensor means; and said actuable means controlling a temperature of each said basin.

11. In a machine for thermally treating a sterile fluid medium in a drape container to permit use of the fluid medium in a surgical procedure, a method for detecting the presence of liquid in said drape container comprising the steps of:

(a) placing on said drape a sensor of liquid in said drape container;

(b) connecting lines from said sensor to a receptacle on said machine; and (c) controlling power to a temperature controller of said drape container based on a signal from said sensor on said drape container.

12. The method of claim 11 wherein step (a) comprises placing on each drape a fiber optic sensor for said drape container machine.

13. The method of claim 11 wherein step (a) comprises placing on said drape a sensor for said drape container to detect conductance between said sensor on said drape and an additional sensor positioned below said drape container.

14. The method of claim 11 wherein step (c) comprises disabling power to a temperature controller of said drape container in response to said sensor not detecting presence of liquid.

15. The method of claim 11 wherein step (c) comprises disabling power to a temperature controller of said drape container in response to said sensor detecting conductance in a range indicative of a leak in said drape container.

16. A device for use in a surgical apparatus to detect a presence of liquid in each of at least one basin comprising a drape, said drape having at least one liquid sensor secured thereto.

17. The device of claim 16 wherein said sensor comprises a fiber optic sensor.

18. The device of claim 16 wherein said sensor comprises means for detecting conductance between said sensor of said drape and an additional sensor affixed to an opposite side of said drape.

19. The device of claim 16 wherein each sensor is connected to a plug permanently affixed to said drape.

20. The device of claim 16 wherein each sensor is connected to a plug detachable from said drape.

21. A method for controlling operation of thermal treatment apparatus in a machine for making a thermally treated fluid medium available in a drape container disposed in a thermally treated basin during a surgical procedure, said method comprising the steps of:

(a) sensing the presence and absence of said sterile medium in said drape container by a sensor disposed within said drape container; and (b) in response to absence of said sterile medium sensed in step (a), automatically disabling the thermal treatment apparatus.

22. A method for controlling operation of thermal treatment apparatus in a machine for making a thermally treated fluid medium available in a drape container disposed in a thermally treated basin during a surgical procedure, said method comprising the steps of:

(a) detecting the presence of said medium in said basin between said drape and said basin by a sensor disposed between said drape and said basin; and (b) in response to detection of said medium in step (a), automatically disabling the thermal treatment apparatus.

* * * * *